(12) United States Patent
Stevenson

(10) Patent No.: US 7,916,013 B2
(45) Date of Patent: *Mar. 29, 2011

(54) RFID DETECTION AND IDENTIFICATION SYSTEM FOR IMPLANTABLE MEDICAL DEVICES

(75) Inventor: Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 665 days.

This patent is subject to a terminal disclaimer.

(21) Appl. No.: 11/307,145

(22) Filed: Jan. 25, 2006

(65) Prior Publication Data

US 2006/0212096 A1 Sep. 21, 2006

Related U.S. Application Data

(60) Provisional application No. 60/594,230, filed on Mar. 21, 2005.

(51) Int. Cl.
*G08B 1/08* (2006.01)
*G08B 23/00* (2006.01)
*A61B 5/00* (2006.01)

(52) U.S. Cl. ............. 340/539.12; 340/572.1; 340/573.1; 600/300; 600/301; 128/903

(58) Field of Classification Search .............. 340/539.12, 340/572.1
See application file for complete search history.

(56) References Cited

U.S. PATENT DOCUMENTS

| | | | |
|---|---|---|---|
| 4,376,441 A | 3/1983 | Duncan | |
| 4,424,551 A | 1/1984 | Stevenson et al. | |
| 4,846,158 A | 7/1989 | Teranishi | |
| 5,333,095 A | 7/1994 | Stevenson et al. | |
| 5,336,158 A | 8/1994 | Huggins et al. | |
| 5,342,408 A * | 8/1994 | deCoriolis et al. | ............... 607/32 |
| 5,855,609 A | 1/1999 | Knapp | |
| 5,905,627 A | 5/1999 | Brendel et al. | |
| 5,963,132 A * | 10/1999 | Yoakum | ..................... 340/572.1 |
| 6,216,038 B1 * | 4/2001 | Hartlaub et al. | ................. 607/31 |

(Continued)

FOREIGN PATENT DOCUMENTS

EP 0 534 782 A1 3/1983

(Continued)

OTHER PUBLICATIONS

U.S. Appl. No. 60/478,717, filed Jun. 16, 2003, Off.

(Continued)

*Primary Examiner* — Donnie L Crosland
(74) *Attorney, Agent, or Firm* — Kelly Lowry & Kelley, LLP

(57) ABSTRACT

A radio frequency identification (RFID) system for use with active implantable medical devices (AIMD) implanted in a patient comprises an interrogator and an RFID tag comprising a substrate, an RFID chip, and an antenna. The RFID is typically enclosed in a biocompatible and hermetically sealed container comprising a ceramic housing, an end cap and an encapsulant. The RFID tag or sealed container may be affixed to an AIMD or surgically implanted in a patient adjacent to an AIMD. Alternatively, the sealed container may be injected into body tissue by a large needle syringe. The RFID tag may store information about an AIMD including manufacturer, model number and serial number. The RFID tag may also store information about a treating physician and/or patient including the treating physician's name and contact information, the patient's name, contact information, medical condition, treatment and other relevant information.

86 Claims, 12 Drawing Sheets

U.S. PATENT DOCUMENTS

| | | | |
|---|---|---|---|
| 6,259,937 B1 * | 7/2001 | Schulman et al. | 600/345 |
| 6,275,369 B1 | 8/2001 | Stevenson et al. | |
| 6,342,839 B1 * | 1/2002 | Curkendall et al. | 340/573.3 |
| 6,375,780 B1 * | 4/2002 | Tuttle et al. | 156/226 |
| 6,566,978 B2 | 5/2003 | Stevenson et al. | |
| 6,765,779 B2 | 7/2004 | Stevenson et al. | |
| 6,957,107 B2 * | 10/2005 | Rogers et al. | 607/60 |
| 7,017,822 B2 | 3/2006 | Aisenbrey | |
| 7,103,413 B2 * | 9/2006 | Swanson et al. | 607/32 |
| 7,174,201 B2 | 2/2007 | Govari et al. | |
| 7,256,695 B2 | 8/2007 | Hamel et al. | |
| 2002/0049482 A1 * | 4/2002 | Fabian et al. | 607/60 |
| 2002/0151770 A1 * | 10/2002 | Noll et al. | 600/300 |
| 2003/0181794 A1 * | 9/2003 | Rini et al. | 600/300 |
| 2005/0247319 A1 * | 11/2005 | Berger | 128/898 |
| 2005/0258242 A1 * | 11/2005 | Zarembo | 235/385 |
| 2006/0183979 A1 * | 8/2006 | Rini et al. | 600/300 |
| 2008/0048855 A1 * | 2/2008 | Berger | 340/539.12 |
| 2008/0065181 A1 * | 3/2008 | Stevenson | 607/115 |

FOREIGN PATENT DOCUMENTS

| | | |
|---|---|---|
| EP | 0 619 101 A1 | 10/1994 |
| WO | WO 96/11722 A1 | 4/1996 |

OTHER PUBLICATIONS

Wesley J. Clement & Bob Stevenson, Determining Effective Loop Area for Use in Industry Standards, May 5, 2005, Abstract: 05-AB-2928-HRS, Heart Rhythm Society.

* cited by examiner

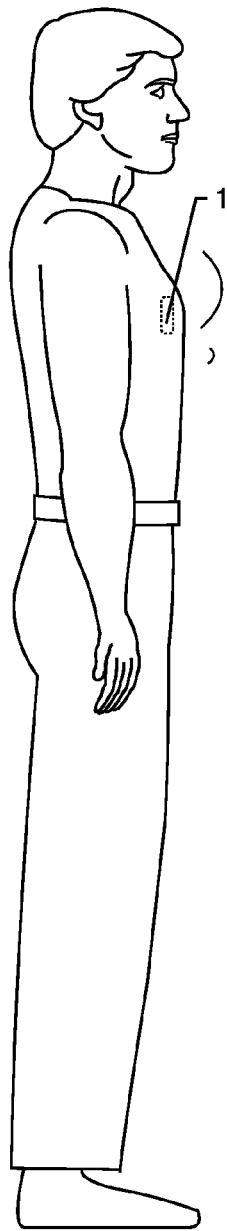
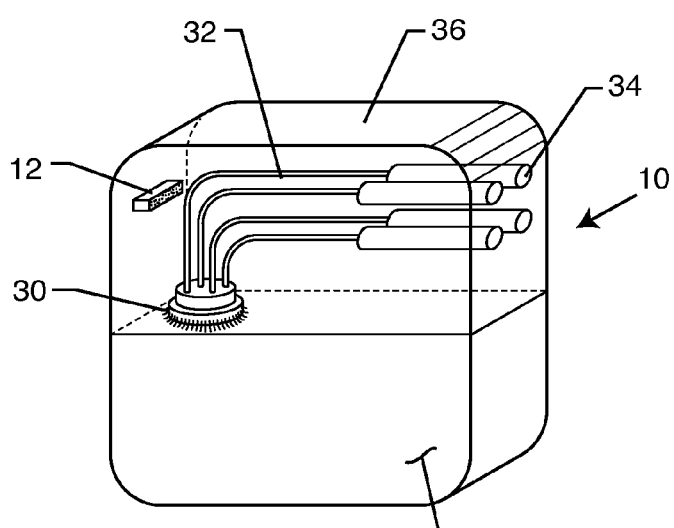
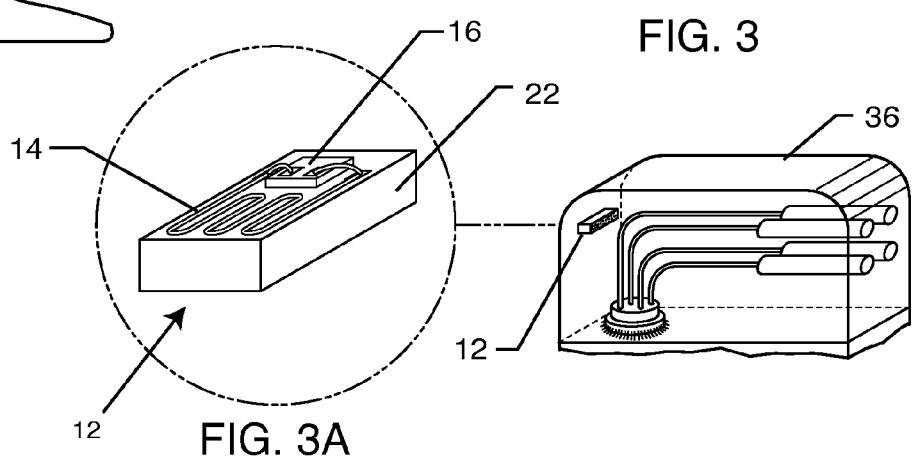

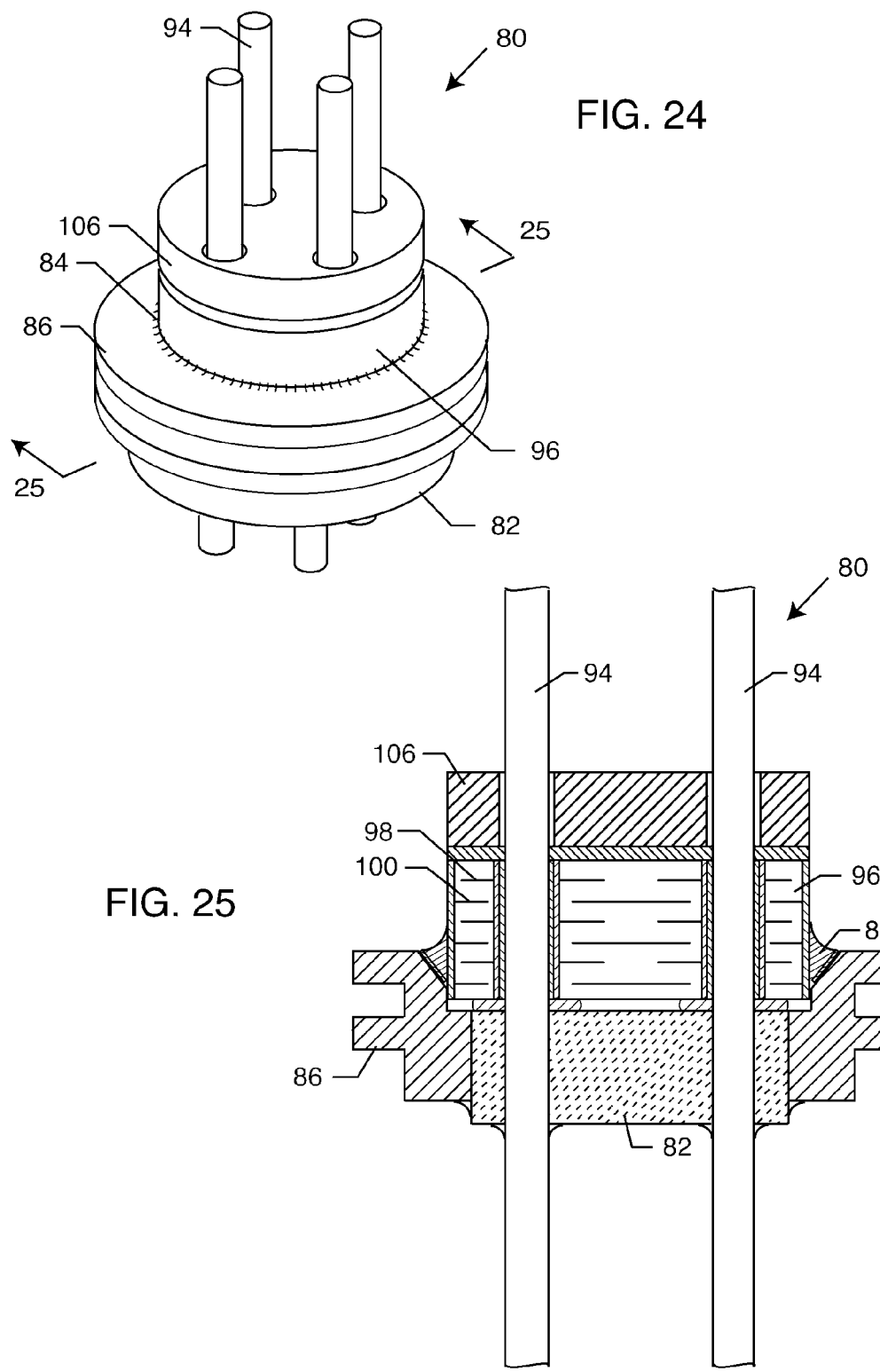

RFID DETECTION AND IDENTIFICATION SYSTEM FOR IMPLANTABLE MEDICAL DEVICES

BACKGROUND OF THE INVENTION

This invention relates generally to methods of identifying implanted medical devices. More specifically, this invention relates to radio frequency identification (RFID) tags for use with medical devices implanted in a patient.

There are known in the art various methods for identifying implanted medical devices. One such method is the use of X-ray identification tags encapsulated within header blocks of pacemakers or implantable cardioverter defibrillators (ICD). Such X-ray identification tags can be read on an X-ray of the implanted device and provide information to the physician. The information so provided is limited due to space and typically includes only the manufacturer and model number of the implanted device. It would be beneficial if physicians were able to obtain additional information about an implanted device and/or a patient from an implanted identification tag. Such beneficial information includes, in addition to the manufacturer and model number of the device, the serial number of the device, the treating physician's name and contact information and, if authorized by the patient, the patient's name, contact information, medical condition and treatment, and other relevant information. Currently, most active implantable medical device (AIMD) patients carry some sort of identification. This could be in the form of a card carried in the wallet or an ID bracelet indicating, for example, that they are a pacemaker wearer of a certain model and serial number. However, such forms of identification are often not reliable. It is quite common for an elderly patient to be presented at the emergency room (ER) of a hospital without their wallet and without wearing any type of a bracelet. In addition, there have been a number of situations where the patient (due to dementia or Alzheimer's, etc.) cannot clearly state that he or she even has a pacemaker. Often times the ER physician will palpitate the patient's chest and feel that there is an implanted device present. If the patient is comatose, has low blood pressure, or is in another form of cardiac distress, this presents a serious dilemma for the ER. At this moment in time, all that the ER knows is that the patient has some sort of an AIMD implant in his or her chest. It could be a pacemaker, a cardioverter defibrillator, or even a vagus nerve stimulator or deep brain stimulator. What happens next is both laborious and time consuming. The ER physician will have various manufacturers' internal programmers transported from the hospital cardiology laboratory down to the ER. ER personnel will then try to interrogate the implantable medical device to see if they can determine what it is. For example, they might first try to use a Medtronic programmer to see if it is a Medtronic pacemaker. Then they might try a St. Jude, a Guidant, and ELA, a Biotronik or one of a number of other programmers that are present. If none of those programmers work, then the ER physician has to consider that it may be a neurostimulator and perhaps go get a Cyberonics or Neuropace programmer.

It would be a great advantage and potentially life saving if the ER physician could very quickly identify the type of implant and model number. In certain cases, for example, with a pacemaker patient who is in cardiac distress, with an external programmer they could boost the pacemaker output voltage to properly recapture the heart, obtain a regular sinus rhythm and stabilize blood pressure. All of the lost time running around to find the right programmer, however, generally precludes this. Accordingly, there is a need for a way to rapidly identify the type and model number of an active implantable medical device so that the proper external programmer for it can be rapidly identified and obtained.

It is already well known in the prior art that RFID tag implants can be used for animals, for example, for pet tracking. It is also used in the livestock industry. For example, RFID tags can be placed in cattle to identify them and track certain information. There is also a preliminary approval from the FDA for an injectable RFID tag into a human. A problem with this has to do with the fact that none of the current RFID tags have been designed to have long term reliability and biocompatibility within the body fluid environment.

Other general methods, none of which are specific to AIMDs, include encapsulating an RFID tag in plastic or placing the RFID tag in a plastic or glass tube with an epoxy infill. However, as will be discussed more fully below, none of these materials provide a truly hermetic seal against body fluids.

It is also important to note that lead wire systems generally remain in the human body much longer than the active implantable medical device itself. For example, in the case of a cardiac pacemaker, the cardiac pacemaker batteries tend to last for 5 to 7 years. It is a very difficult surgical procedure to actually remove leads from the heart once they are implanted. This is because the distal TIP of the lead wires tend to become embedded and overgrown by myocardial tissue. It often takes very complex surgical procedures, including open heart surgery, to remove such lead wire systems. When a pacemaker is replaced, the pectoral pocket is simply reopened and a new pacemaker is plugged into the existing lead wire. However, it is also quite common for lead wires to fail for various reasons. They could fail due to breakdown of electrical insulation or they could migrate to an improper position within the heart. In this case, the physician normally snips the lead wires off and abandons them and then installs new lead wires in parallel with the old abandoned leads. Abandoned lead wires can be quite a problem during certain medical diagnostic procedures, such as MRI. It has been demonstrated in the literature that such lead wires can greatly overheat due to the powerful magnetic fields induced during MRI. Accordingly, it is important that there be a way of identifying abandoned leads and the lead type. Accordingly, there is a need to identify such abandoned lead wires to an Emergency Room physician or other medical practitioner who may contemplate performing a medical diagnostic procedure on the patient such as MRI. This is in addition to the need to also identify the make and model number of the active implantable medical device. It is also important to note that certain lead wire systems are evolving to be compatible with a specific type of medical diagnostic procedure. For example, MRI systems vary in static field strength from 0.5 Tesla all the way above 10 Tesla. A very popular MRI system, for example, operates at 3 Tesla and has a pulse RF frequency of 128 MHz. There are specific certain lead wire systems that are involving in the marketplace that would be compatible with only this type of MRI system. In other words, it would be dangerous for a patient with a lead wire designed for 3 Tesla to be exposed to a 1.5 Tesla system. Thus, there is also a need to identify such lead wire systems to Emergency Room and other medical personnel when necessary. For example, a patient that has a lead wire system that has been specifically designed for use with a 3 Tesla MRI system may have several pacemaker replacements over the years.

Identification of abandoned lead wires in a patient is also quite important. It has been shown in the past that abandoned lead wires can over heat during MRI procedures. This is particularly true of cardiac lead wires. Lead wires are abandoned for a variety of reasons. Sometimes lead wires will fail or lose contact, for example with the myocardial tissue of the right ventricle. It is a very difficult procedure for a surgeon to remove abandoned lead wires. Such procedures often involve open heart surgery. The reason for this is that after leads have been in place for a long time they tend to become overgrown and encapsulated with myocardial tissue. When a physician encounters one or more defective lead wires it is easier to clip them off and leave them hanging in the pectoral pocket and insert brand new lead wires through the venous system into the right ventricle and in parallel with the old abandoned lead or leads. However, such abandoned lead wires that are not terminated can lead to over heating during MRI procedures. The ANSI/AAMI PC69 task force recently did a study by going to various medical centers around the United States and tracing actual patient X-rays. This data was published at the annual Heart Rhythm Society in New Orleans in May 2005. Reference: Heart Rhythm 2005 abstract tracking number 05-AB-2928-HRS. Therefore, it is a feature of the present invention that the novel hermetically sealed RFID chip with fixation device can be used to attach to one or more abandoned leads in the pectoral pocket. This is very useful whether or not the patient receives a new pacemaker or AIMD, implant or not. That is, if we have a patient that has reverted to normal sinus rhythm and no longer needs a pacemaker and has abandoned leads, the radiology department can quickly tell through the RFID scan whether or not abandoned lead wires are present. As mentioned, this is extremely important to prevent inadvertent MRI on such a patient. In the past, it has been shown that abandoned leads can heat up so much that ablation of cardiac tissue and even perforation of cardiac walls can occur. It is, therefore, a feature of the present invention that both the lead wire system and the AIMD can be separately identified.

Accordingly, there is a need for an improved medical identification tag that can store additional information about an implanted device and/or a patient, without unduly increasing the size of the identification tag or jeopardizing the operation of the implanted device or the health of the patient, while providing a better hermetic seal.

The present invention meets these needs by providing an RFID tag that can be enclosed within an AIMD or introduced into a patient's body adjacent to an AIMD. The RFID tag of the present invention is capable of storing information about the medical device, the physician, and the patient, as described above.

SUMMARY OF THE INVENTION

The present invention is directed to a system for identifying implants within a patient, comprising an implantable medical device, a radio frequency identification (RFID) tag having an antenna and being associated with the implantable medical device, the RFID tag containing information relating to the patient and/or the implantable medical device, and an interrogator capable of communicating with the RFID tag.

Such implantable medical devices may include active implantable medical devices (AIMD) such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device and component parts thereof, including lead wires or abandoned lead wires. The active implantable medical device may include a non-metallic header block in which the RFID tag is implanted.

The present invention optionally includes a biocompatible and hermetically sealed container in which the RFID tag is disposed. The container may comprise a housing, and an encapsulant made of a thermal-setting polymer or a silicone material within the housing surrounding at least a portion of the RFID tag. The housing is typically manufactured of ceramic, glass, porcelain, sapphire and composites thereof, or specialty polymer composites. Further, a desiccant, also known as a moisture getter, may be disposed within the housing adjacent to the RFID tag. The container may further include a biocompatible end cap hermetically sealed to the housing. The container may also include a fixation hole for affixing the container to body tissue and an optional X-ray identification tag.

The RFID tag may be read-only or readable/writable. The interrogator may be a reader/writer device and may be in communication with a computer or computer network.

The present invention is also direct to a process for manufacturing the radio frequency identification (RFID) device for identifying the implant within a patient. The process comprises the steps of:

associating an RFID tag with an active implantable medical device;

storing information relating to the patient or the active implantable medical device on the RFID tag; and implanting the RFID tag in the patient.

The process may further comprise the step of embedding the RFID tag in a header block of the active implantable medical device, or encasing the RFID tag in a biocompatible and hermetically sealed container including a ceramic housing and an encapsulant within the housing surrounding at least a portion of the RFID tag. The encapsulant may be comprised of a thermal-setting polymer or a silicone material. An end cap may be hermetically sealed to the housing. The container may also include a fixation hole for affixing the container to body tissue and an X-ray identification tag.

These and other aspects of the invention will be apparent to one skilled in the art in light of the following detailed description of the preferred embodiments.

BRIEF DESCRIPTION OF THE DRAWINGS

The accompanying drawings illustrate the invention. In such drawings:

FIG. 1 is a depiction of a patient with an AIMD fitted with an RFID tag of the present invention and an external interrogator/reader.

FIG. 2 is an isometric view of a typical AIMD fitted with a biocompatible enclosed RFID tag of the present invention.

FIG. 3 is an isometric view that isolates the header block of the AIMD shown in FIG. 2 and a close-up view of the embedded RFID tag.

FIG. 24 is a perspective view of a quadpolar feedthrough capacitor combined with a lossy ferrite inductor slab.

FIG. 25 is an enlarged sectional view taken generally along the line 25-25 of FIG. 24.

DETAILED DESCRIPTION OF THE PREFERRED EMBODIMENTS

The present invention is directed to a radio frequency identification (RFID) system for use with active implantable medical devices (AIMDs) and an associated RFID tag. Specifically, the RFID system comprises an RFID tag implanted in a patient's body and associated with an implanted AIMD, and an interrogator in communication with the RFID tag.

Figure 4:
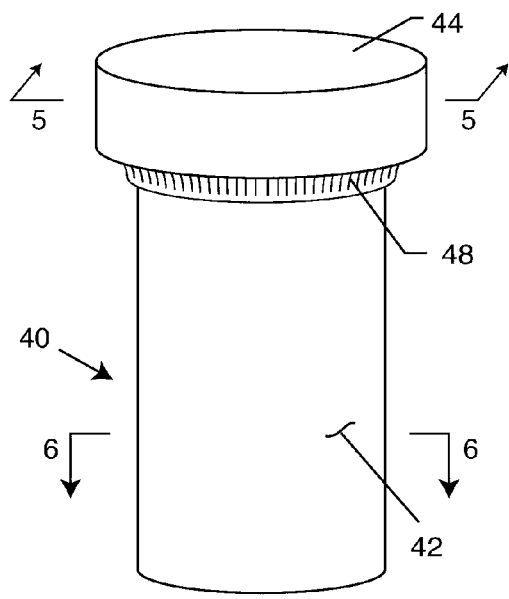
FIG. 4 is an isometric view of a biocompatible and hermetically sealed container in accordance with the present invention.

FIG. 1 is an outline drawing of an adult male pacemaker patient with an AIMD 10. FIG. 2 is an isometric view of an AIMD or pacemaker 10 that has been fitted with an RFID tag 12 of the present invention. In a preferred embodiment, as shown in FIG. 3, the RFID tag 12 comprises a substrate 22, an antenna or coil 14 and an RFID chip 16. These components of the RFID tag 12 are well known in the art. RFID standards are evolving worldwide at various frequencies. For example, a 915 MHz protocol is generally evolving to be used for retail goods and inventory control. However, due to the high frequency, the 915 MHz protocols are not very useful for human implants. The reason for this is that humans are largely water and 915 MHz fields are greatly affected by the presence of water. The preferred embodiment is another RFID protocol which operates at 13.56 MHz which is ideal for an implantable RFID tag. The 13.56 MHz lower frequency will readily penetrate and communicate with the tag instead of reflecting off of the skin surface or being absorbed. There are other lower frequency RFID systems, for example, in the 130 kHz range which would also be suitable. In alternate embodiments, the RFID tag 12 may be enclosed in a biocompatible and hermetically sealed container 40 as shown in FIG. 4 and as will be described more fully below.

FIG. 1 shows a dashed ellipse which indicates one potential location for an AIMD 10. The location shown in FIG. 1 is typical of a right or left pectoral muscle implant. Right and left pectoral muscle implants are typical for a cardiac pacemaker or implantable cardioverter defibrillator (ICD). The right and left pectoral muscle region is chosen due to the easy access to the subclavian veins for insertion of lead wires and electrodes down into the heart. The present invention may also find application in AIMDs such as, an implantable defibrillator, a congestive heart failure device, a hearing implant, a cochlear implant, a neurostimulator, a drug pump, a ventricular assist device, a drug pump, a spinal cord stimulator, an implantable sensing system, a deep brain stimulator, an artificial heart, an incontinence device, a vagus nerve stimulator, a bone growth stimulator, a gastric pacemaker, or a prosthetic device.

Referring once again to FIG. 1, one can see an interrogator 20, also known as a hand held scanner or reader. The interrogator 20 transmits an electromagnetic field pulse 26 which is intercepted by the antenna 14 that is part of the implanted RFID tag 12. The implanted RFID tag 12 is generally passive. That means that it does not have its own self-contained source of energy such as a battery. The electromagnetic field 26 that comes from the interrogator 20 resonates with the antenna 14 and RFID chip 16 providing energy for the RFID chip 16 to generate a signal and the antenna 14 to emit a return pulse 28. This pulse 28 is picked up by an antenna 14 in the interrogator 20. The pulse 28 contains digital modulation. As previously described, this digital modulation can contain information such as the model number of the patient's AIMD, the serial number of the AIMD, the manufacturer of the lead wire system, the name of patient's physician, and contact information for the physician. In addition, if the patient authorizes, the digital pulse can also contain the patient's name, the patient's medical condition, the patient's address and telephone number, and other pertinent information.

FIG. 2 is an isometric view of a typical AIMD 10, such as a cardiac pacemaker. Cardiac pacemakers typically have a metallic housing 18 which can be of titanium, stainless steel or the like. This metallic housing 18 is laser welded shut and generally contains a hermetic feedthrough terminal 30 for passage of lead wires 32 into the interior of the metallic housing 18. Said hermetic feedthrough terminals 30 are well known in the art and are generally laser welded into the metallic housing 18 of the implantable medical device. The lead wires 32 as shown in FIG. 2, are generally routed to connectors 34. The connectors 34 provide a convenient location to plug in the lead wires 32 which are routed to the heart for pacing and biologic sensing. The connector assembly 30, 32, 34 is generally encapsulated within a molded non-metallic, i.e., plastic or ceramic, header block 36, as shown. Usually, this header block 36 is of clear casting materials which are well known in the art. Opaque thermal setting or chemically setting materials may also be used.

Referring once again to FIG. 2, there is an RFID tag 12 which has been cast into the header block 36. Not shown are suitable fixtures used to position the connectors 34 and RFID tag 12 during the casting of the header block 36. The RFID tag 12 shown in FIG. 2 may be enclosed within a biocompatible and hermetically sealed container 40 as mentioned above and as will be described below.

FIG. 3 isolates the header block 36 of FIG. 2 with an RFID tag 12 embedded within the header block 36. In this case, the RFID tag 12 is not enclosed within a biocompatible and hermetically sealed container 40. As shown in FIG. 3A, the RFID tag 12 a substrate 22, an antenna 14, and an RFID chip 16. The substrate 22 may comprise single or multiple layers. The antenna 14 is for both receiving electromagnetic energy to power the RFID chip 16 and for retransmitting a digital pulse. These devices are well known in the art.

FIGS. 2 and 3 both show a non-hermetically sealed RFID tag 12 which is encapsulated within the molded header block of an AIMD such as a cardiac pacemaker. Such molded header blocks are common in the industry and are designated by ISO Standards IS-1, DF-1 or IS-4 or the equivalent. These header blocks 36 typically contain a connector system so that the medical practitioner can plug in lead wires for example those that would run from the pacemaker into the chambers of the heart. Referring to FIG. 2 one can see that this header block material is a solid encapsulated material such as an epoxy, thermal setting polymer or the like. In general such materials are not considered truly hermetic and will have leak rates varying from $10^{-5}$ to $10^{-6}$ cubic centimeters per second. Accordingly, if such active implantable medical device as shown in FIG. 2 were implanted for long periods of time, then body fluids would eventually, due to the bulk permeability of the header block 36 material reach the electronic circuits of the RFID tag 12. Body fluids are comprised primarily of water and dissolved salts including sodium, chlorine, potassium, calcium and the like. These are ionic and if they reach the surfaces of the RFID tag 12 it will readily short it out. Thus, in the preferred embodiment as will be described herein, the RFID tag 12 will be hermetically sealed. However, a short term medical implant device placement of the RFID chip within the header block 36 would be acceptable. For example, the average life of most cardiac pacemakers is five to seven years. The lead wires are left in place while pacemakers are replaced as their batteries deplete. Accordingly, in the present invention it would be acceptable to place a non-hermetically sealed RFID tag 12 into an encapsulated header block as shown in FIG. 3 as long as this was not designed for a long term implant. Long term implants would include cochlear implants, certain neurostimulators or Bions which could be in the human body for forty years or longer, and the like.

The hermetic seal characteristics of the header block assembly 36 depend upon the ability of the molding or plastic materials of the header block 36 to prevent body fluids from penetrating to the RFID tag 12. Penetration of body fluids over time to the RFID tag 12 may cause degradation of insulation resistance, or short circuits. Accordingly, hermetically encapsulating the RFID tag 12, as will be described below, is the preferred embodiment.

FIG. 4 is an isometric view of a biocompatible and hermetically sealed container 40 in accordance with the present invention. This hermetically sealed container 40 is designed to encase the RFID tag 12. Since the RFID tag 12 is generally constructed of materials that are not long term biocompatible and body fluid resistant, it is important to prevent body fluids from reaching the RFID tag 12. Even if the RFID tag 12 is embedded deeply within a molded polymer header block 36 as illustrated in FIG. 3, when such a device is implanted into body tissue for many years (cochlear implants may last forty years or longer), moisture can slowly penetrate due to the bulk permeability of the polymer material of the header block 36. In the art, this is known as the leak rate or hermeticity of a device. Generally speaking, adjunct sealants, polymers and the like are not considered truly hermetic. A leak rate of $10^{-9}$ cubic centimeters per second or slower is required to assure that moisture will not penetrate to sensitive electronics over long periods of time. In order to achieve such low leak rates, generally glass seals or gold brazed ceramic seals are required. It is well known that brazed ceramic seals are generally superior to fused or compression glass seals.

The marginal hermeticity of certain glass seals is demonstrated by antique marine floats that were used to hold fishing nets. These generally consisted of hollow glass spheres or balls which were filled with air. Now that many years have passed, many of these hollow glass spheres are partially filled with water. This is an example of how water can penetrate through glass given enough time due to the bulk permeability of the glass itself. Dense ceramic materials, such as alumina, generally do not allow this water penetration.

Prior art RFID chips that are used for both animal and sometimes for human implant have a serious deficiency in that they are not truly hermetically sealed. These devices often use a cylindrical glass cup which is filled with epoxy or other type polymer materials such as silicone or the like. A deficiency with such seals as mentioned above is, that over long periods of time, moisture will slowly penetrate and reach sensitive electronic circuits. When moisture reaches electronic circuits under low bias voltage conditions, dendrites and tin whiskers can form thereby shorting out or reducing insulation resistance to electronic components. There is another problem of great concern and that is not all of the materials that are used within the RFID chip itself (for example within the ASIC electronics) are biocompatible. Therefore, moisture intrusion over long periods of time can lead to issues with toxicity to surrounding tissues as these non-biocompatible materials leach out. Accordingly, it is the preferred embodiment of the present invention that the RFID chip be completely hermetically sealed with a maximum leak rate of $1 \times 10^{-7}$ cubic centimeters per second. As used herein "hermetically sealed" means a leak rate of $10^{-7}$ cubic centimeters per second or slower. In fact, in the preferred embodiment as described in FIGS. 4-10 a maximum leak rate of no more than $1 \times 10^{-12}$ cubic centimeters per second is ideal. This is in sharp contrast to prior art polymer fill systems which achieve at most a leak rate of around $1 \times 10^{-5}$ cubic centimeters per second, and are not considered hermetic seals in accordance with the present invention.

Figure 5:
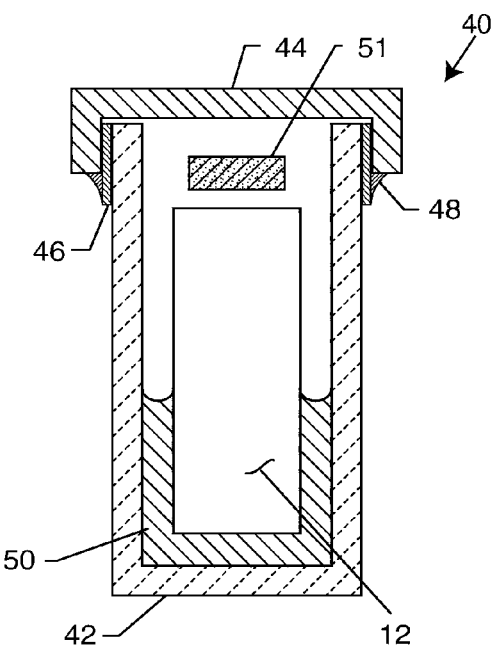
FIG. 5 is a vertical cross-section of the biocompatible and hermetically sealed container taken along line 5-5 of FIG. 4.

Referring now back to FIGS. 4 and 5, the RFID tag 12 has been placed inside the biocompatible and hermetically sealed container 40. This sealed container 40 has an extruded, machined, or pressed ceramic housing 42. It is not possible to make the entire sealed container 40 out of a metal such as titanium because this would shield the RFID tag 12 from the electromagnetic field from the interrogator 20. In other words, if the RFID tag 12 was placed inside the titanium housing of an AIMD 10, this would shield the radio frequency pulses. This would completely prevent the RFID tag 12 from receiving energy or sending out any pulses. Accordingly, the ceramic housing 42 as indicated in FIGS. 4 and 5, allows electromagnetic fields to freely pass to and from the RFID tag 12.

The ceramic housing 42 as shown in FIG. 5, is formed by ceramic manufacturing operations that are well known in the art. This generally consists of taking pure alumina ceramic powders, formulating them with a binder system and pressing them into the desired shape. This is then fired or sintered at very high temperature which makes a very hard structure. In a preferred embodiment, the housing 42 is hermetically sealed using an end cap 44 that covers an open end of the housing 42. In FIG. 5, the end cap 44 is constructed from titanium but may also be ceramic. The ceramic housing 42 is first selectively metallized using a sputtering technique. A preferred methodology would be to sputter a titanium-molybdenum composition 46 which is suitable for wetting a gold braze joint 48. There are also a number of other methods of providing metallization on ceramic tubes, which are well known in the art and would provide a suitable surface for gold brazing. The gold brazed joint 48 is used to make a metallurgical hermetic connection between the end cap 44 and the ceramic housing 42.

Referring once again to FIG. 5, the RFID tag 12 is in an encapsulant 50 so that it will not rattle around or vibrate inside the overall sealed container 40. Such encapsulant 50 can be of a variety of non-conductive materials, including thermal-setting nonconductive polymers, silicones and the like. There is also a desiccant material 51 that is placed inside the device as a moisture getter. Some background is needed in order to better understand this. In a relatively large implantable medical device such as a cardiac pacemaker, there is a significant amount of open air space inside of the device. This is typically backfilled with dry nitrogen or the like. Because of the relatively large amount of open air space, the hermetic terminal for ingress and egress of lead wires through the device can have a leak rate of from $10^{-7}$ to $10^{-9}$ cubic centimeters per second. This allows a certain amount of moisture to penetrate over a period of years. In other words, when a small amount of moisture enters into a relatively large available space, droplets or moisture thin films will not typically be formed. The moisture will disburse and will gradually raise what is called the residual moisture (humidity) level inside the device. The residual moisture level typically starts at zero and will slowly climb over the life of the device to around 8%. However, in a relatively tiny hermetically sealed space as shown in the hermetically sealed enclosure of FIG. 5 there is much less available free air space. Accordingly, the hermetic seal that is formed with gold braze 48 in the enclosure in FIG. 5 preferably would have a lower leak rate. In the preferred embodiment, it is anticipated that these devices will be tested to a leak rate of no more than $1 \times 10^{-12}$ cubic centimeters per second. This means that much less moisture will penetrate the device and there will be much less chance for a moisture thin film or droplet to form on the sensitive electronic circuits. The desiccant material 51 has been added as a safety mechanism such that hermetic terminals having a leak rate in the approximate range of $1 \times 10^{-7}$ to $1 \times 10^{-9}$ cubic centimeters per second can be safely used. That is any residual moisture over a long period of time tending to enter the same space as the hermetically sealed RFID tag 12 would be entrapped with the desiccant material 51 and have very little chance to form a moisture thin film or droplet which could lead to dendrite growth or failure of the electronic circuits. Desiccants are generally well known in the prior art and can include anhydrous magnesium and calcium sulfate. Also activated silica gels are commonly used. Other acceptable desiccants include molecular sieves, montmorillonite clay activated carbons and synthetic sodium aluminosilicate. All of these desiccants have a very strong affinity for water and also absorb moisture mounting to more than 20% of their original weight.

Figure 6A:
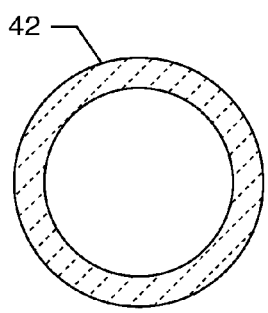
FIG. 6A is a horizontal cross-section of the biocompatible and hermetically sealed container taken along line 6-6 of FIG. 4.
Figure 6C:
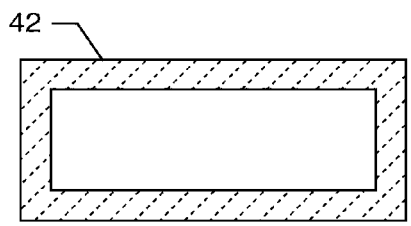
FIG. 6C is a horizontal cross-section of a rectangular alternative of the biocompatible and hermetically sealed container taken along line 6-6 of FIG. 4.
Figure 6B:
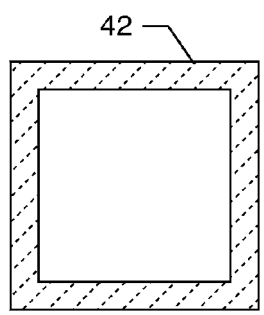
FIG. 6B is a horizontal cross-section of a square-shaped alternative of the biocompatible and hermetically sealed container taken along line 6-6 of FIG. 4.
Figure 6D:
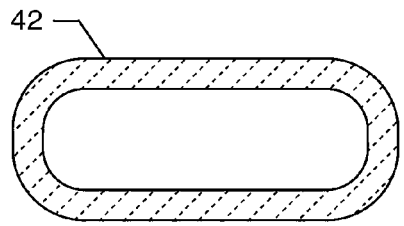
FIG. 6D is a horizontal cross-section of an elliptical or oval alternative of the biocompatible and hermetically sealed container taken along line 6-6 of FIG. 4.

FIGS. 6A-6D show cross-sectional views of various alternative shapes for the ceramic housing 42 and end cap 44 previously described in FIG. 5. FIG. 6A is a round cross-section, which is identical to that previously shown in FIG. 5. An alternative square cross-section is shown in FIG. 6B. A rectangular cross-section is shown in FIG. 6C. An elliptical or oval cross-section is shown in FIG. 6D. All the configurations and others will be apparent to those skilled in the art.

Figure 7:
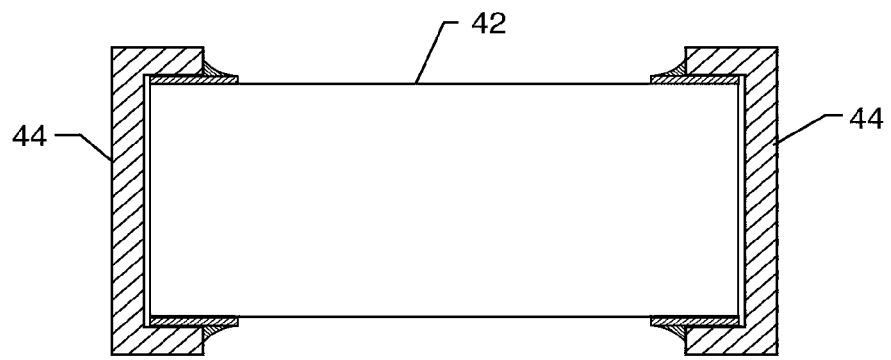
FIG. 7 is a vertical cross-section of an alternative construction of the biocompatible and hermetically sealed container of the present invention.

FIG. 7 is a very similar biocompatible and hermetic sealed container 40 as previously described in FIGS. 5 and 6; however, in this case, the ceramic housing 42 is open at both ends and two end caps 44 hermetically seal the container 40. The reason for this is that the ceramic housing 42 may be extruded in a continuous operation and then blade cut. This could make the ceramic housing 42 much less expensive than the closed end housing 42 previously shown in FIG. 5. A negative of the assembly as described in FIG. 7 is that there are two end caps 44 which must be gold brazed or welded 48 to the ceramic housing 42. Accordingly, there must be two circumferential or perimeter metallized bands 46 of the ceramic housing 42 so that the gold braze 48 will wet and form a hermetic seal. It is a matter of manufacturing cost trade-offs whether to use the single end cap 44 assembly as described in FIG. 5 or the dual end cap 44 assembly as shown in FIG. 7.

It should also be mentioned that the end caps 44 may be of titanium, stainless steel, tantalum, niobium or other suitable biocompatible metallic material. There are also a number of ceramic materials that may be used for the end cap 44, including alumina ceramic and the like. However, in order to form the gold braze joint 48, a ceramic end cap 44 may also have to be selectively metallized 46 by sputtering, plating, vapor deposition or the like. There are also a number of alternative materials that may be used for the hermetic housings 42 as described herein. These include all ceramic, glasses, sapphire, porcelain, polymer composites and the like.

Figure 8:
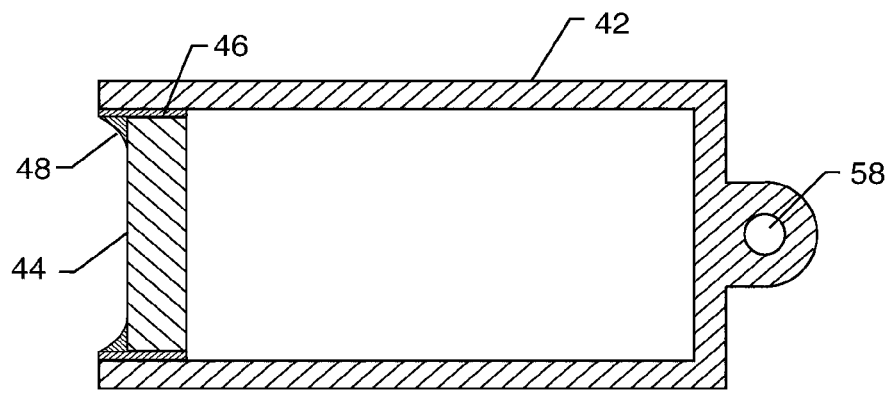
FIG. 8 is a vertical cross-section of another alternative construction of the biocompatible and hermetically sealed container of the present invention.
Figure 9:
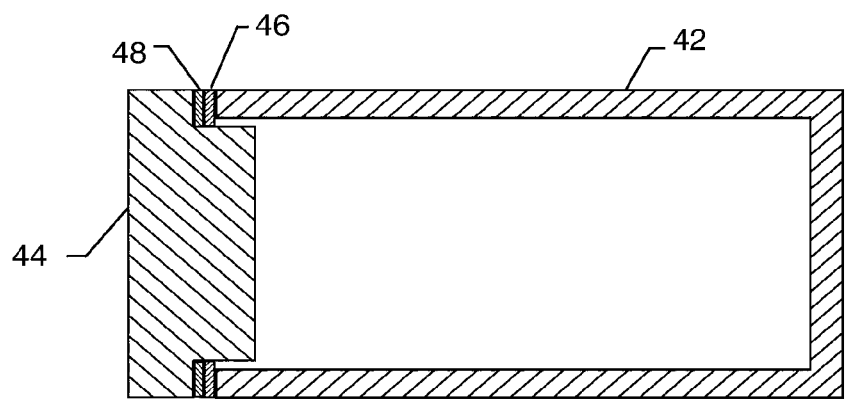
FIG. 9 is a vertical cross-section of yet another alternative construction of the biocompatible and hermetically sealed container of the present invention.

FIG. 8 is an alternative method of installation of an end cap 44 wherein the end cap 44 is placed inside of the ceramic housing 42. FIG. 9 is yet another method of having a step titanium end cap 44 with a gold braze joint 48 between the butt ends of the ceramic housing 42 and the step of the end cap 44. Referring once again to FIG. 8, one can see that there is a novel hole 58 convenient for placing a suture. This could be used to affix the hermetically sealed RFID tag to any point within the human body. This suture hole 58 can also be used to affix the RFID tag to an active or abandoned lead wire system. This is important for the purposes of identifying the type of lead wire system and its compatibility with certain medical diagnostic procedures, such as certain types of MRI systems.

Figure 10:
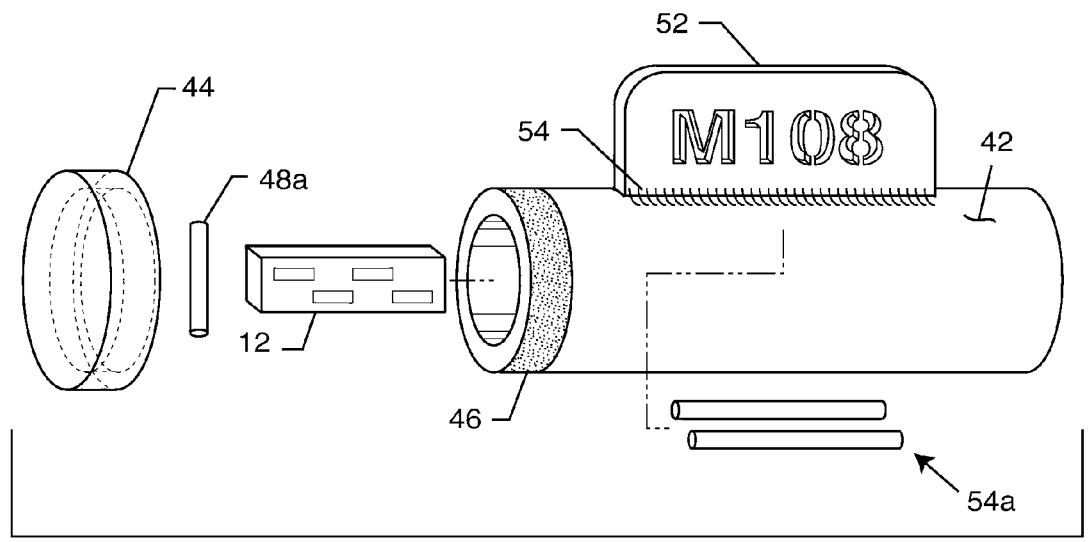
FIG. 10 illustrates the assembly of the biocompatible and hermetically sealed container of the present invention including an X-ray identification tag.

FIG. 10 is an exploded view of the sealed container 40 of FIGS. 4 and 5. The RFID tag 12 is positioned for insertion into the ceramic housing 42. After the RFID tag 12 is inserted and encapsulated, a gold braze pre-form 48a is positioned near the joint of the end cap 44 and the ceramic housing 42 as shown. An optional X-ray identification tag 52 may also be affixed to the sealed container 40 with more gold braze pre-forms 54, as shown. The gold braze pre-forms 48a and 54 are re-flowed in a vacuum brazing furnace. When the assembly is placed into the vacuum brazing furnace, the gold braze pre-form 48a seals the end cap 44 to the ceramic housing 42 and the one or more gold braze pre-forms 54 attach the X-ray identification tag 52 to the ceramic housing 42. Low temperature brazes are preferred so as not to cause thermal damage to the RFID tag. As previously described, the ceramic housing 42 is selectively metallized 46 using sputtering or equivalent techniques prior to placement in the vacuum brazing furnace so that the gold braze pre-forms 48a and 54 will wet to the ceramic tube 42. Suitable low temperature brazes include Ti—Cu—SiI, Cu—SiI and the like.

X-ray identification tags 52 are well known in the art for encapsulating with pacemaker and ICD header blocks. The reason for the X-ray identification tag 52 is so that a physician can read a patient chest X-ray and obtain valuable information such as pacemaker model number and manufacturer. Having a redundant identification system like this is desirable in the very unlikely event that the RFID tag 12 should fail to operate.

Figure 11:
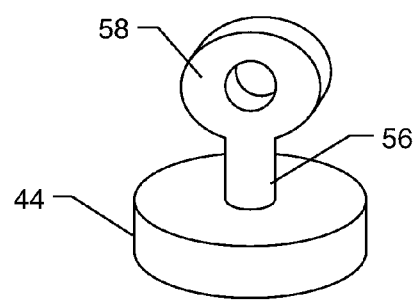
FIG. 11 is an isometric view of an alternative tissue fixation end cap for use with the biocompatible and hermetically sealed container of the present invention.

FIG. 11 is a novel end cap 44 that is formed with a fixation hole comprising a post 56 and a loop 58. This end cap 44 is designed so that a surgeon can put a suture or stitch through the loop 58 and affix the container 40 to body tissue. This is very important in cases where a container 40 is to be implanted adjacent to a prosthetic device or outside of the AIMD 10. Certain AIMDs 10, such as deep brain or neurostimulators, are simply too small or do not have a header block 36 into which to encapsulate or capture the container 40. In this case, during surgery, a loop 58 as shown in FIG. 11 allows a convenient location for the physician to stitch and fixate the container 40. The hole feature 58 as shown in FIG. 11, can be used to stitch or fix any of the containers of the present invention to body tissue, such as muscle tissue, a ligament, a rib or the like. As previously mentioned, feature 58 can also be used to affix any of the embodiments of the present invention to active or abandoned lead wire systems for AIMDs.

In most cases, the container 40 is about the size of two grains of rice. Accordingly, if the container 40 were simply placed into the body without fixation, it could migrate through muscle or other tissues. This would make it very difficult to locate for purpose of use or if it was later desired to remove it.

Figure 12:
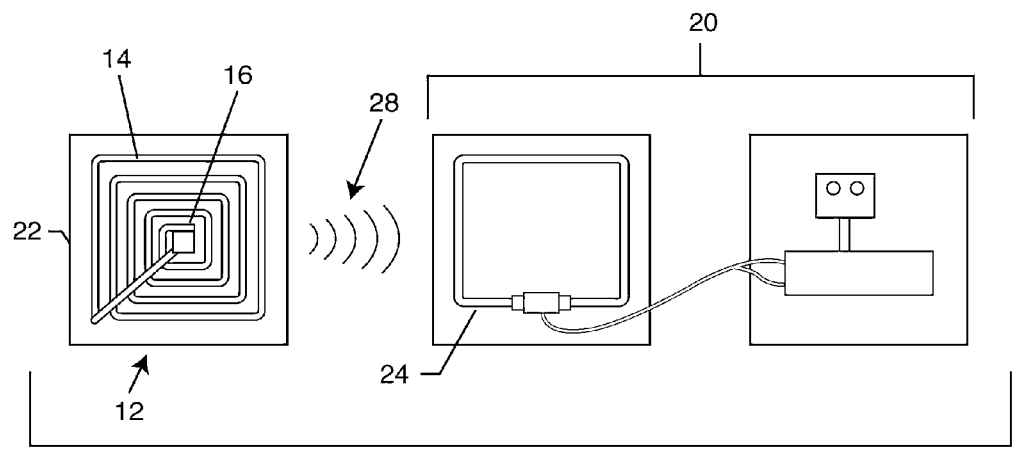
FIG. 12 is a block diagram depicting operation of a system including the RFID tag of the present invention.
Figure 13:
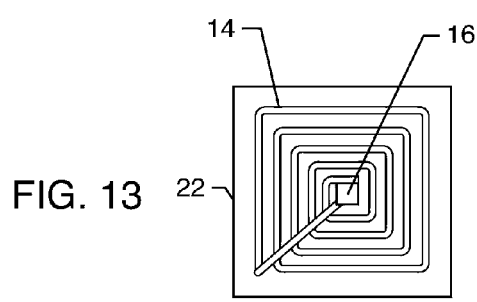
FIG. 13 is a top view of an RFID tag and antenna of the present invention.
Figure 14:
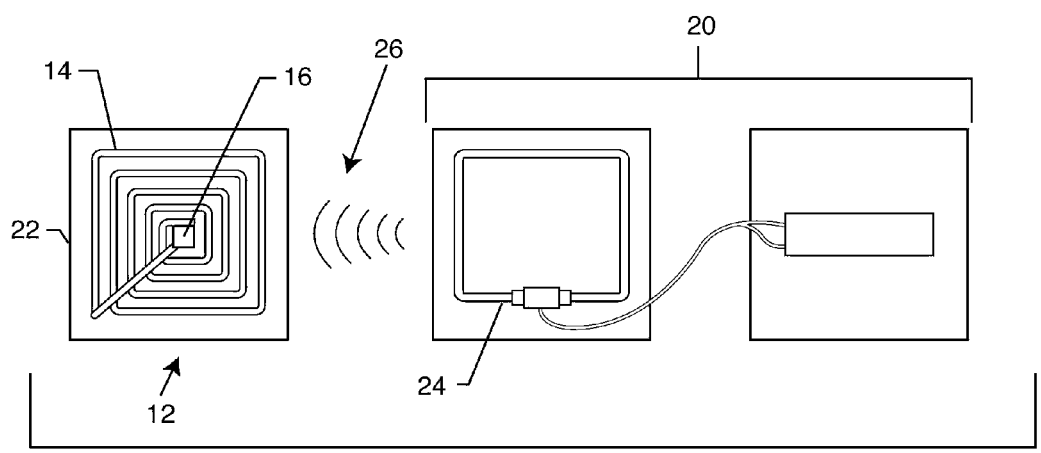
FIG. 14 is a block diagram depicting operations of an alternative system including an RFID tag of the present invention.

FIGS. 12, 13 and 14 depict block diagrams of the RFID system in operation. As described above, the RFID tag 12 consists of a substrate 22, an RFID chip 16, and an antenna 14. The interrogator 20 with associated antenna 24 discharges electromagnetic energy 26 to the antenna 14 of the RFID tag 12, which powers up the RFID chip 16 and allows it to produce the electromagnetic return signal 28, as shown. The electromagnetic return signal 28 is detected by the interrogator 20 and presented as a digital code sequence. The RFID tag 12 may be read-only (RO) or read/write (RW). With an RW RFID tag 12, a physician may use an external programmer or interrogator 20 to write additional patient information to the RFID tag 12. This additional information may include patient name, patient address, medical condition, and so on. In the case of an RO RFID tag 12, the RFID tag 12 would be installed at the time of AIMD manufacture and would designate manufacturer, model number and other key information. However, an RO RFID tag 12 would not be later programmable and could not include added important information such as patient name, doctor name, patient diagnosis and so forth. The interrogator 20 may comprise programmer or programmer/reader, which would permit direct display of all of the information contained on the RFID tag 12.

Figure 15:
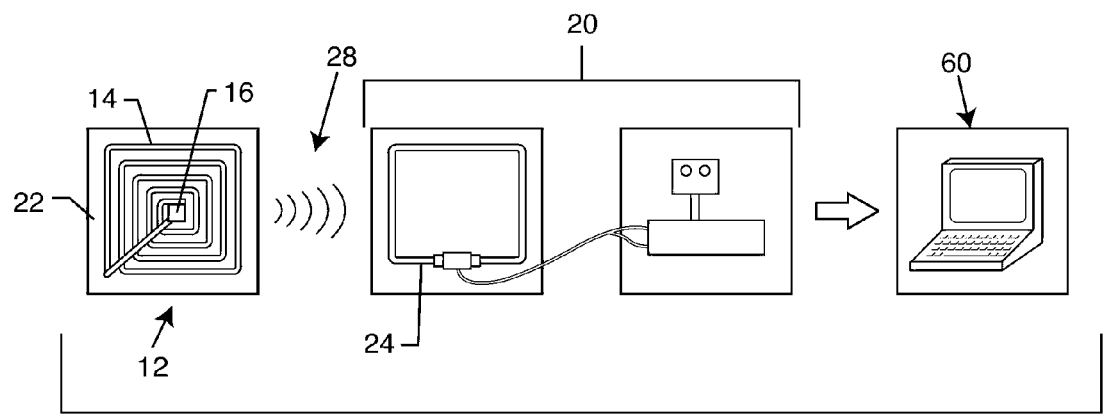
FIG. 15 is a block diagram depicting operation of another alternative system including an RFID tag of the present invention.

FIG. 15 illustrates a very similar system as previously described in FIGS. 12, 13 and 14 except that the interrogator 20 is designed to be integrated with a computer system 60 which may be linked to the worldwide web. In this case, a unique digital number transmitted by the RFID tag 12 may be entered into the computer system 60. The computer system 60 maintains a database of important information that is all keyed to the digital information transmitted by the RFID tag 12. In this way, the physician or emergency room personnel may obtain the digital code from the RFID tag 12 which enters automatically (or manually) into the computer system 60 to immediately get a download, including all of the information required as to the model and serial number of the AIMD, lead wire system, patient and physician information, and patient history when available. The RFID tag could also access the new American College of Cardiology National Cardiovascular Data Registry (ACC-NCDR). ACC-NCDR is a comprehensive cardiac and date repository for three national registries: the CathPCI Registry, the CarotidStent Registry, and the ICD Registry. The ICD Registry was developed in partnership with the Heart Rhythm Society and is designed for participation by hospitals. It collects detailed information on ICD implantations and has as one of its missions helping hospitals meet regulatory requirements and Medicare requirements.

Figure 16:
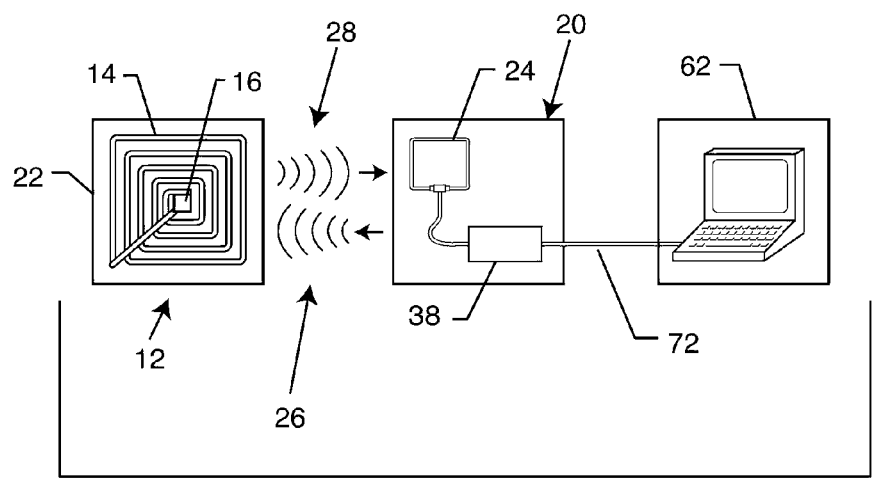
FIG. 16 is a block diagram depicting operation of yet another alternative system including an RFID tag of the present invention.

FIG. 16 illustrates a system very similar to that described in FIG. 15 except that the output of the interrogator 20 would go to an antenna and processor 38 which are designed to be linked directly to a laptop computer 62. This could also be done by USB or equivalent cable interface network 72. The laptop computer 62 may contain a full database by model numbers and serial numbers of medical implantable devices. A drawback to this type of system is that it would be very difficult to keep updated with current patient and physician information.

Figure 17:
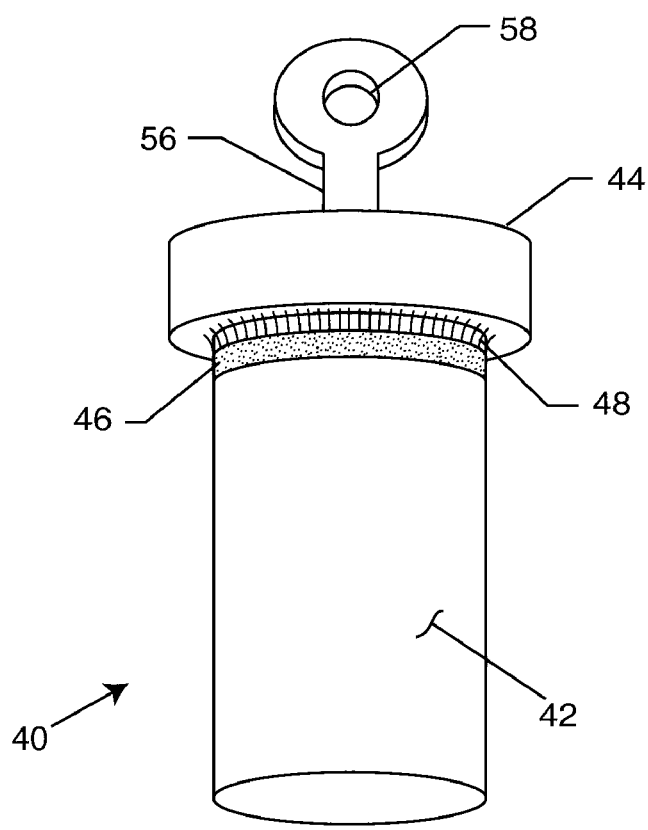
FIG. 17 is an isometric view of an alternative embodiment of the biocompatible and hermetically sealed container of the present invention.
Figure 17A:
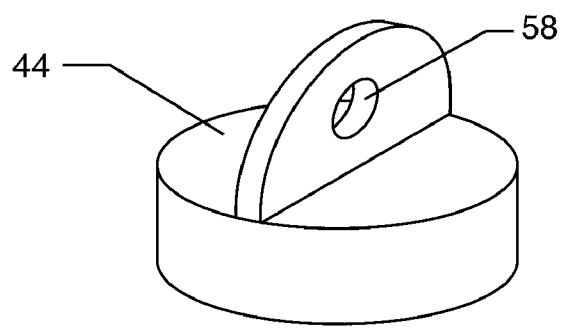
FIG. 17A is an isometric view of another alternative end cap for use with the biocompatible and hermetically sealed container of the present invention.

FIG. 17 is an isometric view of the RFID tag 12 that was previously described in FIGS. 4 and 5, but has been modified in accordance with the end cap 44 described in FIG. 11. The titanium end cap 44 includes a loop 58 to fix in body tissue or affix to an active or abandoned lead wire set. The metallization 46 on the ceramic housing 42 and the braze 48 forms a hermetic seal. The style of post 56 and loop 58 depicted is just one type one with ordinary skill in the art will recognize. As an alternative, FIG. 17A shows another embodiment. It will be obvious to those skilled in the art that loops 58 may also be placed directly on the ceramic housing 42 itself.

Figure 18:
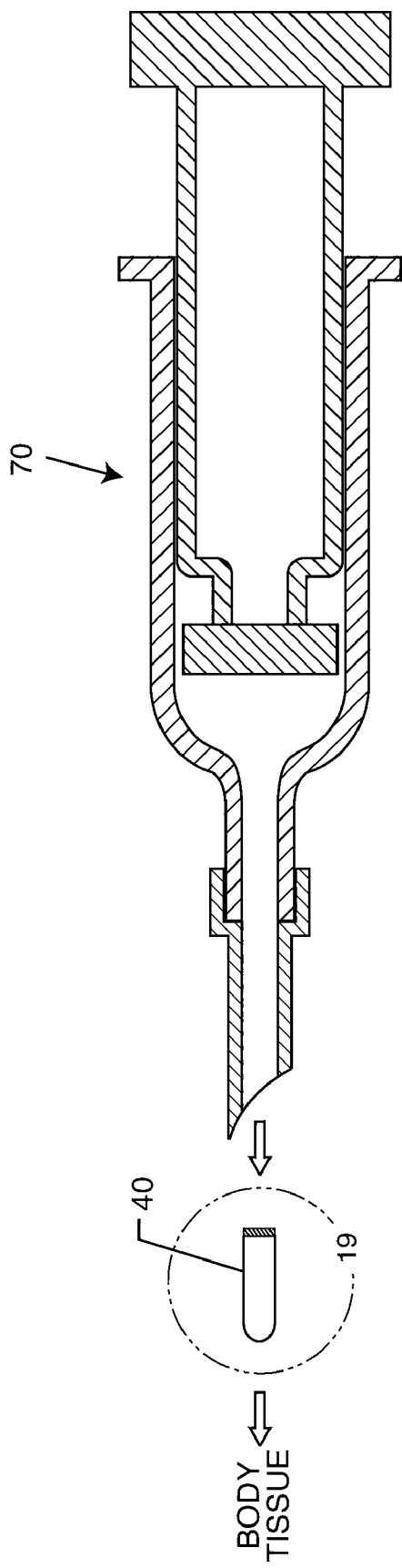
FIG. 18 is a cross-sectional view of a large needle syringe and biocompatible and hermetically sealed container of the present invention.

FIG. 18 illustrates a large needle syringe 70 designed for injecting the RFID tag container 40 directly into body tissue. In this case, the sealed container 40 has an end cap 44 that is designed to make a smooth transition from the ceramic housing 42 to the end cap 44. This makes the container 40 suitable for injection into body tissue. As previously mentioned, a negative to this approach is that the container 40 may tend to migrate over time within the body tissue.

Figure 19:
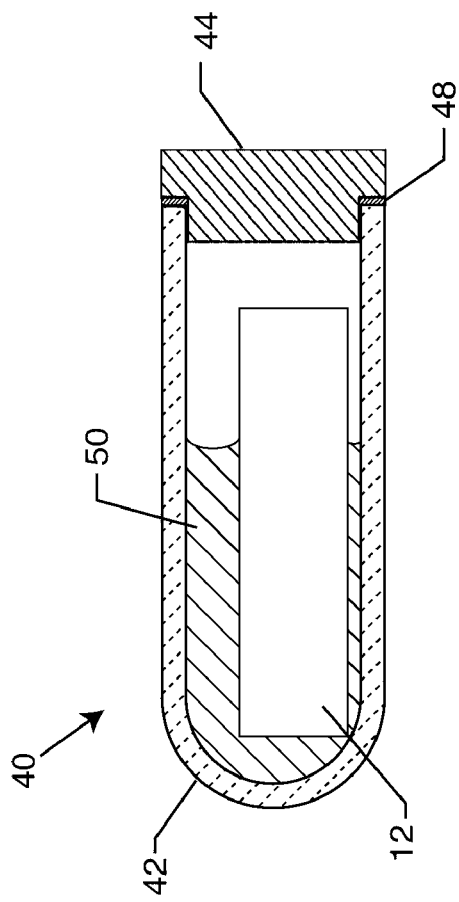
FIG. 19 an enlarged cross-sectional view of the encapsulated RFID tag in the biocompatible and hermetically sealed container depicted in FIG. 18.

FIG. 19 is an exploded view taken from FIG. 18 illustrating a cross-section of the container 40. The titanium end cap 44 has been butted onto and brazed 48 to the ceramic tube 42 such that it forms a smooth outer surface.

Figure 20:
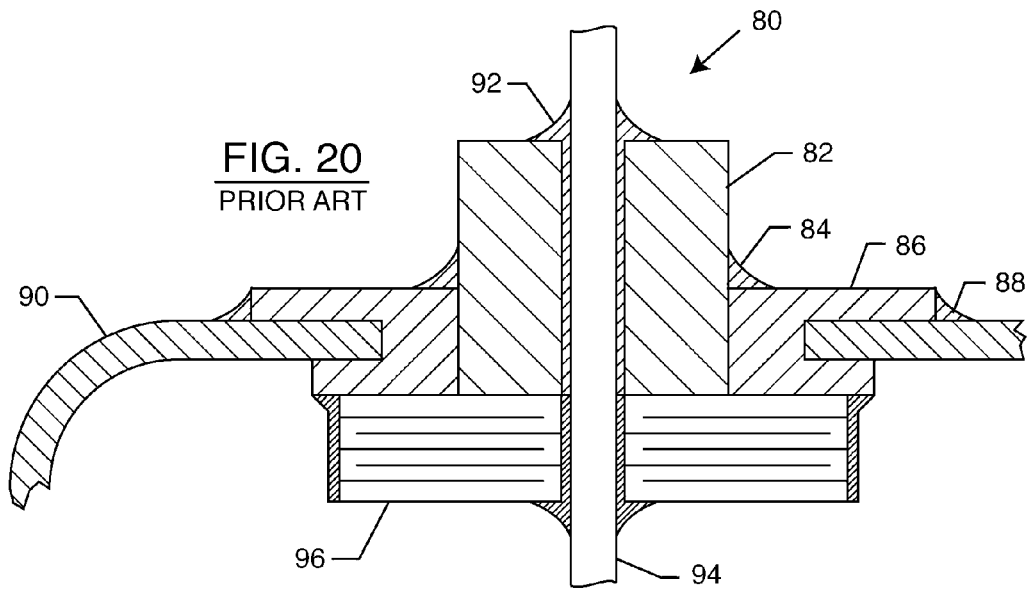
FIG. 20 is a fragmented sectional view of a prior art unipolar hermetic terminal typically used in active implantable medical devices.

FIG. 20 illustrates a prior art unipolar hermetic terminal 80 typically used in active implantable medical devices. Hermetic terminals consist of an alumina insulator 82 which is gold brazed 84 to a ferrule 86. In turn, the ferrule is typically laser welded 88 to the titanium housing 90 of an active implantable medical device. There is also a hermetic seal 92 that is formed between the alumina insulator 82 and the lead wire 94. This is typically also done by gold brazing, glass sealing or the like. There is also a prior art ceramic feedthrough capacitor 96 shown co-bonded to the hermetic terminal subassembly. Such feedthrough capacitors 96 are well known in the prior art for decoupling and shielding against undesirable electromagnetic interference (EMI) signals, such as those produced by cellular telephones, microwave ovens and the like. See, for example, U.S. Pat. Nos. 4,424,551; 5,333,095; 5,905,627; 6,275,369; 6,566,978 and 6,765,779.

Figure 21:
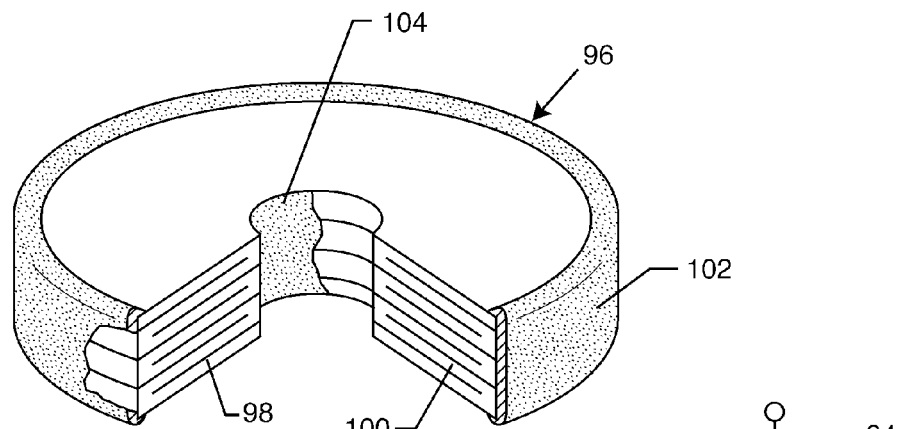
FIG. 21 is an enlarged, partially fragmented perspective view of the feedthrough capacitor shown in FIG. 20.

FIG. 21 is a partial cutaway view showing the details of the prior art feedthrough capacitor 96 as previously illustrated in FIG. 20. One can see that it has internally embedded electrode plate sets 98 and 100. Electrode plate set 100 is known as the ground electrode plate set and is coupled to the capacitor's outside diameter metallization 102. The active electrode plate set 98 is electrically connected to the capacitor inside diameter metallization 104.

Figure 22:
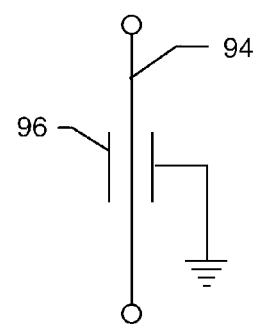
FIG. 22 is a schematic electrical diagram of the coaxial feedthrough capacitor of FIG. 20.

FIG. 22 is a schematic diagram of the prior art feedthrough capacitor 96 illustrated in FIGS. 20 and 21.

The present invention resides in RFID readers and systems in order to interrogate and identify an active implantable medical device. In order for the RFID field to be able to read a tag embedded within the human body, it must generate a very powerful yet relatively low frequency field. As previously described, the preferred embodiment is a 13.56 MHz HF reader. Such readers are most effective when held within 10 centimeters of the implant. In general, these are 3 to 6-watt effective radiated power (ERP) devices. In comparison, a cellular telephone which produces a very powerful near field is only a 0.6 to 2-watt ERP devices. Accordingly, the patient with an active implantable medical device is subjected to a very powerful digitally pulsed RFID reader field. Accordingly, it is a feature of the present invention that the AIMD have very robust shielding and filtering against the electromagnetic interference that is being produced by the RFID reader itself. This is in order to assure that the electronics of the AIMD are not subjected to temporary or permanent malfunction. Instances of pacemaker inhibition, microprocessor reset or even permanent damage to device electronics have all been documented in the past due to EMI. Accordingly, there is a need in combination with the present invention for the AIMD to be particularly robust so it will be resistant to the fields produced by the RFID reader.

ANSI/AAMI Standard PC69 defines electromagnetic compatibility test requirements for pacemakers and implantable defibrillators. It specifically has a radiated dipole test with a mandatory requirement that the AIMD be resistant when the dipole has 40 milliwatts of net input power. There is also an optional or voluntary test level which is at 8 watts (and 2 watts at certain higher frequencies). PC69 currently covers the frequency range from 450 MHz to 3 GHz which is, of course, above the range of the preferred embodiment 13.56 MHz RFID readers. Because of this, AIMDs tend to use relatively low value feedthrough capacitors as illustrated in FIGS. 20 and 21. Such feedthrough capacitance values, for example, can be as low as 300 picofarads and still comply with the mandatory 40-milliwatt level. However, recent testing at Mount Sinai Medical Institute in Miami indicates that pacemakers that do not have a feedthrough capacitor EMI filter to comply with the optional 8-watt level can respond to the signals from RFID readers. Periods of noise sensing, inhibition and misbeats were documented in pacemakers out to a distance of 21 centimeters. This is the distance between the pacemaker placed in a saline tank and a portable RFID reader.

Accordingly, it would be preferable to use much higher value feedthrough capacitors than shown in FIGS. 20, 21 and 22. Unfortunately, it is impractical to indefinitely raise the amount of capacitance value for the feedthrough capacitor. This is because too much capacitance can seriously load down the output of the AIMD. In addition, there is usually insufficient space inside of the AIMD to place too large of a capacitor. Also, large values of capacitance can cause excessive currents to flow in implanted lead wires during MRI procedures.

Figure 23:
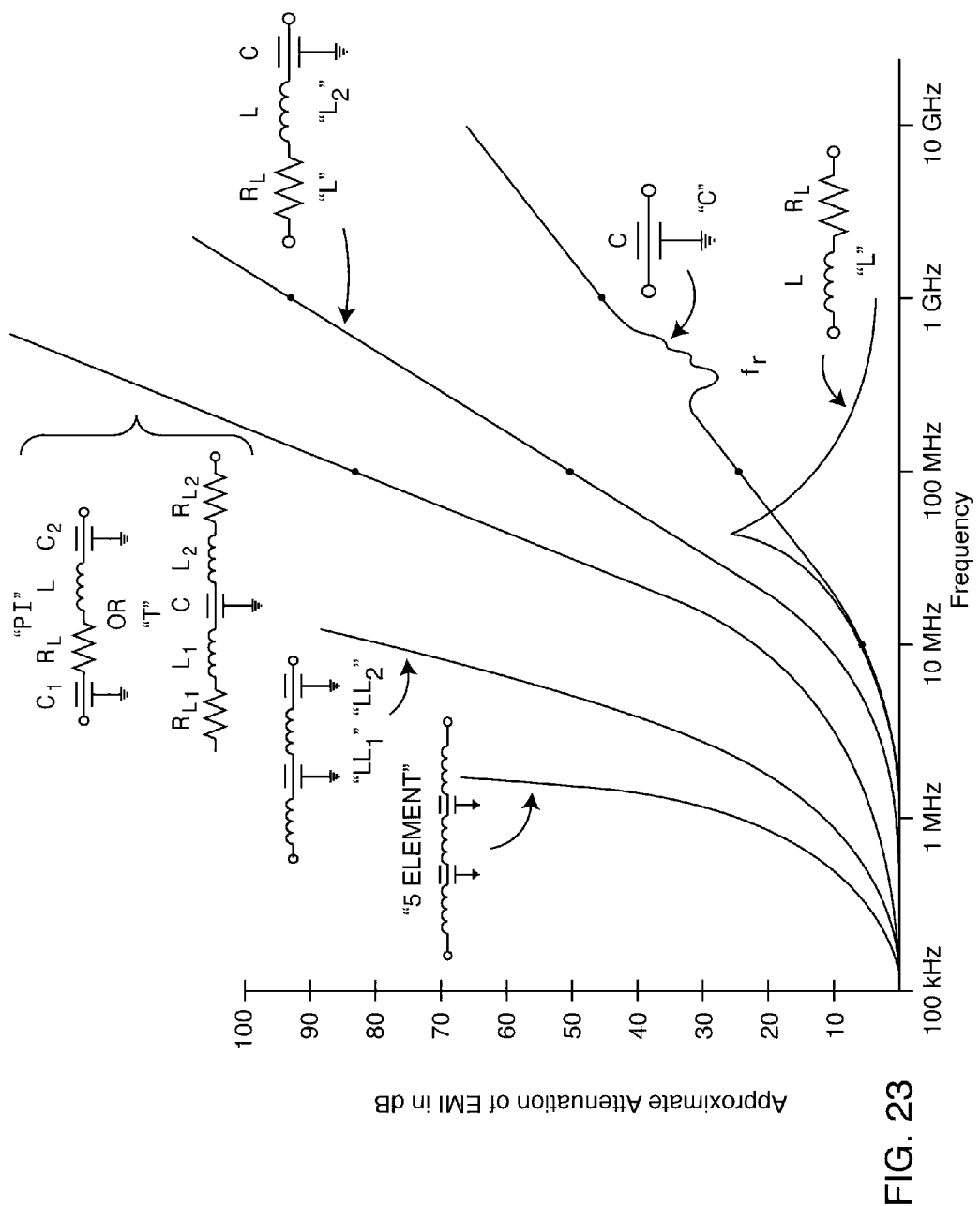
FIG. 23 illustrates various EMI attenuation curves for several different multi-element EMI filters.

A better way to approach this is illustrated in FIG. 23 and is more fully described in co-pending patent application Ser. No. 11/097,999, and U.S. Pat. No. 6,999,818, the contents of which are incorporated herein. Such describe the advantages of using multi-element EMI filters. Referring to FIG. 23, one can see that the prior art feedthrough capacitors "C" have an attenuation slope shown as C. The average attenuation slope rate for this is only 20 dB per decade. By adding additional series elements, such as inductive and resistive elements, one can greatly increase the attenuation slope rate of the EMI filter. For example, referring to the $L_1$ or $L_2$ curve of FIG. 23, one can see that the attenuation slope rate has increased to 40 dB per decade. This makes for a much more efficient EMI filter. Calling attention to the $LL_1$ or $LL_2$ curve, one can see that the attenuation slope rate has gone up dramatically. In this case, it is 80 dB per decade. This is a much more efficient use of the volume and weight available inside of an implantable medical device.

FIGS. 24 and 25 illustrate a quadpolar feedthrough capacitor 96 which is combined with a lossy ferrite inductor slab 106. This allows the designer to use a relatively low value of capacitance such that it does not load down the output of the AIMD or degrade biologic sensing signals, but at the same time by adding the inductor element, offers a filter with a very high degree of RF immunity. In this way, one can comply with the optional 8-watt level of PC69 and provide immunity to closely held RFID tag readers while not overloading the AIMD circuitry. Too much capacitance on the output of the AIMD also tends to lower its input impedance at MRI RF pulsed frequencies. Accordingly, it is important that the capacitance value also be kept low for this reason.

Figure 26:
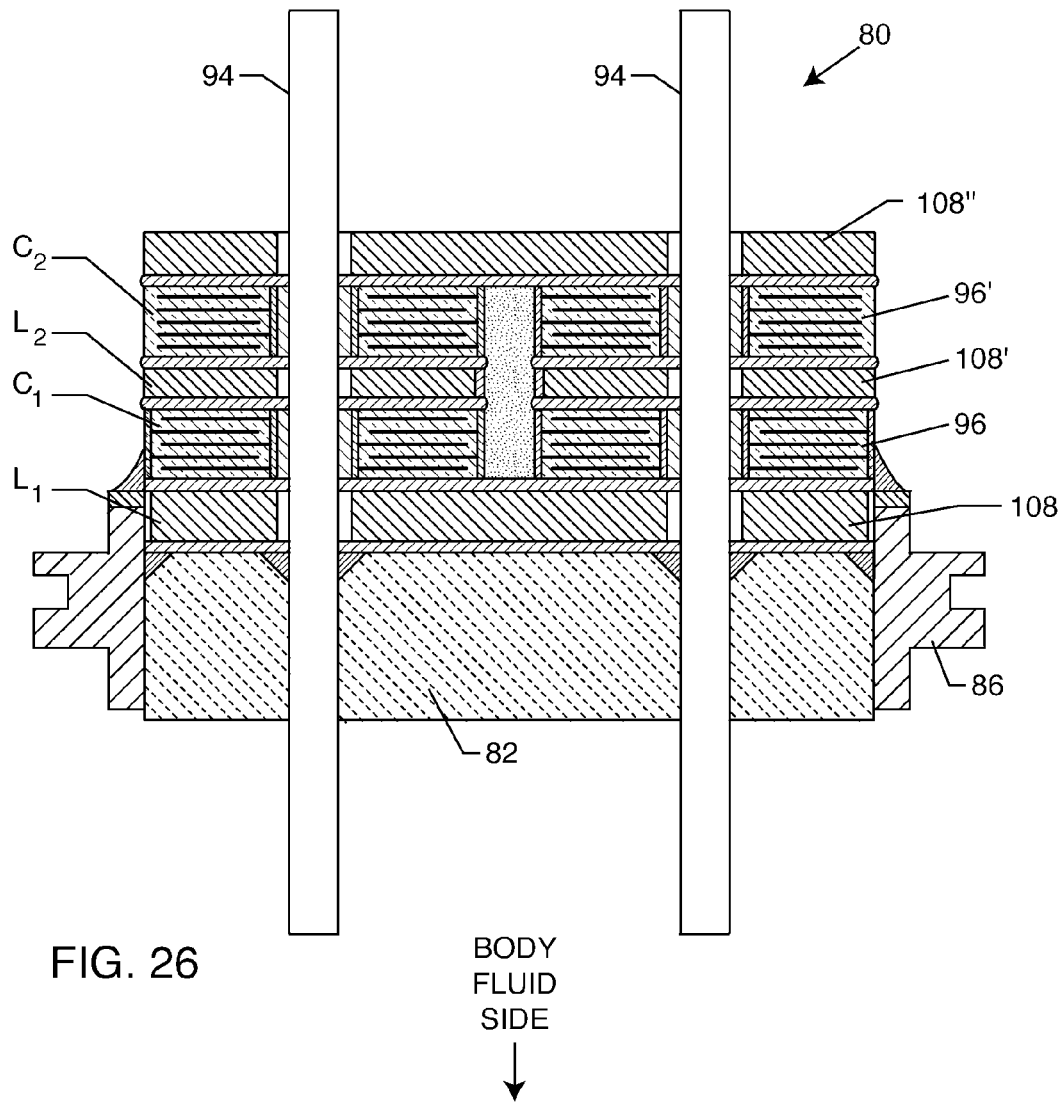
FIG. 26 is a sectional view similar to FIG. 25 illustrating a quadpolar feedthrough filter terminal constructed in an LL configuration.
Figure 27:
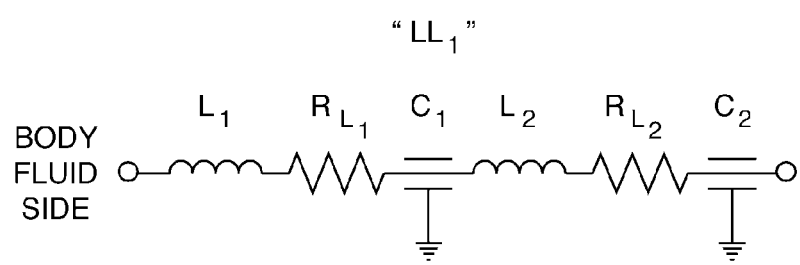
FIG. 27 is an electrical schematic diagram of the feedthrough terminal illustrated in FIG. 26.

FIGS. 26 and 27, show a terminal 80 in an $LL_1$ configuration. Referring once again to FIG. 23, one can see that this has an attenuation slope rate of 80 dB per decade which is extremely robust. In point of fact, in combination with the present invention such that the AIMD be resistant to RFID readers in the preferred embodiment, the EMI filter circuit would be modified to be of the L, T or LL configuration.

Although various embodiments have been described in detail for purposes of illustration, various modifications may be made without departing from the scope and spirit of the invention.

What is claimed is:

1. A system for identifying implants within a patient, comprising:
    an implantable medical device;
    a hermetically sealed radio frequency identification (RFID) tag associated with the implantable medical device, the RFID tag containing information relating to the patient and/or the implantable medical device, wherein a hermetically sealed container in which the RFID tag is disposed, is biocompatible and has a leak rate of no more than $10^{-9}$ cubic centimeters per second; and
    an interrogator capable of communicating with the RFID tag.

2. The system of claim 1, wherein the implantable medical device comprises an active implantable medical device including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires or abandoned lead wires.

3. The system of claim 1, wherein the RFID tag includes an antenna.

4. The system of claim 1, wherein the implantable medical device includes a header block and the RFID tag is implanted in the header block.

5. The system of claim 1, wherein the hermetically sealed container has a leak rate of no more than $10^{-12}$ cubic centimeters per second.

6. The system of claim 1, wherein the container comprises a housing taken from the group including ceramic, glass, porcelain, sapphire and composites thereof, and specialty polymer composites.

7. The system of claim 6, including a desiccant within the housing.

8. The system of claim 6, wherein the container comprises an encapsulant within the housing surrounding at least a portion of the RFID tag.

9. The system of claim 8, wherein the encapsulant is comprised of a thermal-setting polymer or a silicone material.

10. The system of claim 1, wherein the container further includes an end cap hermetically sealed to the housing.

11. The system of claim 1, wherein the container further includes a fixation hole for affixing the container to body tissue, an implantable device, or a lead wire.

12. The system of claim 1, further comprising an X-ray identification tag associated with the biocompatible and hermetically sealed container.

13. The system of claim 1, wherein the RFID tag is read-only or readable/writable.

14. The system of claim 13, wherein the interrogator is a read only or a reader/writer device.

15. The system of claim 14, wherein the interrogator is in communication with a computer or computer network.

16. The system of claim 1, wherein a radio frequency of between 132 kHz and 915 MHz is used to communicate with the RFID tag.

17. The system of claim 16, wherein the radio frequency used to communicate with the RFID tag is approximately 13.56 MHz.

18. A system for identifying implants within a patient, comprising:
an active implantable medical device;
a hermetically sealed radio frequency identification (RFID) tag associated with the active implantable medical device, the RFID tag including an antenna and containing information relating to the patient and/or the active implantable medical device, wherein the RFID tag is read-only or readable/writable;
a biocompatible and hermetically sealed container in which the RFID tag is disposed, wherein the container comprises a housing, an encapsulating within the housing surrounding at least a portion of the RFID tag, and an end cap hermetically sealed to the housing, wherein the container has a leak rate of no more than $10^{-9}$ cubic centimeters per second; and
an interrogator capable of communicating with the RFID tag.

19. The system of claim 18, wherein the interrogator is a reader/writer device.

20. The system of claim 19, wherein the interrogator is in communication with a computer or computer network.

21. The system of claim 18, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires or abandoned lead wires.

22. The system of claim 18 wherein the active implantable medical device includes a header block and the RFID tag is implanted in the header block.

23. The system of claim 18, wherein the encapsulant is comprised of a thermal-setting polymer or a silicone material.

24. The system of claim 18, wherein the container further includes a fixation hole for affixing the container to body tissue, an implantable device, or a lead wire.

25. The system of claim 18, further comprising an X-ray identification tag affixed to the biocompatible and hermetically sealed container.

26. The system of claim 18, wherein the hermetically sealed container has a leak rate of no more than $10^{-12}$ cubic centimeters per second.

27. The system of claim 18, wherein a radio frequency of between 132 kHz and 915 MHz is used to communicate with the RFID tag.

28. The system of claim 27, wherein the radio frequency used to communicate with the RFID tag is approximately 13.56 MHz.

29. A system for identifying implants within a patient, comprising:
an active implantable medical device including a header block;
a radio frequency identification (RFID) tag disposed within the header block, the RFID tag containing information relating to the patient and/or the active implantable medical device, wherein the header block has a leak rate of no more than $10^{-9}$ cubic centimeters per second; and
an interrogator capable of communicating with the RFID tag.

30. The system of claim 29, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires or abandoned lead wires.

31. The system of claim 29, wherein the RFID tag includes an antenna and is read-only or readable/writable, the interrogator is a reader/writer device, and wherein the interrogator is in communication with a computer or computer network.

32. The system of claim 29, further comprising an X-ray identification tag associated with the RFID tag.

33. The system of claim 29, wherein a radio frequency of between 132 kHz and 915 MHz is used to communicate with the RFID tag.

34. The system of claim 33, wherein the radio frequency used to communicate with the RFID tag is approximately 13.56 MHz.

35. A process for manufacturing a radio frequency identification device (RFID) for identifying an implant within a patient, comprising the steps of:
associating a hermetically sealed RFID tag with an implantable medical device;
embedding the RFID tag in a header block of an active implantable medical device, wherein the header block has a leak rate of no more than $10^{-9}$ cubic centimeters per second;
storing information relating to the patient or the implantable medical device on the RFID tag; and
implanting the RFID tag in the patient.

36. The process of claim 35, further comprising the step of encasing the RFID tag in a biocompatible container including a housing taken from the group including ceramic, glass, porcelain, sapphire and composites thereof, and specialty polymer composites.

37. The process of claim 36, including a desiccant within the housing.

38. The process of claim 36, including an encapsulant within the housing surrounding at least a portion of the RFID tag.

39. The process of claim 38, wherein the encapsulant is comprised of a thermal-setting polymer or a silicone material.

40. The process of claim 36, further comprising the step of hermetically sealing an end cap to the housing.

41. The process of claim 36, wherein the container further includes a fixation hole for affixing the container to body tissue.

42. The process of claim 36, further comprising the step of affixing an X-ray identification tag to the container.

43. The process of claim 35, wherein the active implantable medical device comprises an active implantable medical device including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device, and component parts thereof, including lead wires and abandoned lead wires.

44. The process of claim 35, including using a radio frequency of between 132 kHz and 915 MHz to communicate with the RFID tag.

45. The process of claim 44, wherein the radio frequency used to communicate with the RFID tag is approximately 13.56 MHz.

46. A process for manufacturing a radio frequency identification device (RFID) for identifying an implant within a patient, comprising the steps of:
associating an RFID tag with an active implantable medical device;
storing information relating to the patient or the active implantable medical device on the RFID tag;
encasing the RFID tag in a biocompatible and hermetically sealed container including a housing and an encapsulant within the housing surrounding at least a portion of the RFID tag, wherein the header block has a leak rate of no more than $10^{-9}$ cubic centimeters per second;
embedding the RFID tag in a header block of the active implantable medical device; and
implanting the RFID tag in the patient.

47. The process of claim 46, wherein the container comprises a housing taken from the group including ceramic, glass, porcelain, sapphire and composites thereof, and specialty polymer composites.

48. The process of claim 47, including a desiccant within the housing.

49. The process of claim 46, wherein the encapsulant is comprised of a thermal-setting polymer or a silicone material.

50. The process of claim 46, further comprising the step of hermetically sealing an end cap to the housing.

51. The process of claim 46, wherein the container further includes a fixation hole for affixing the container to body tissue.

52. The process of claim 46, further comprising the step of affixing an X-ray identification tag to the container.

53. The process of claim 46, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device, and component parts thereof, including lead wires and abandoned lead wires.

54. The process of claim 46, wherein the hermetically sealed container has a leak rate of no more than $10^{-12}$ cubic centimeters per second.

55. The process of claim 46, including using a radio frequency of between 132 kHz and 915 MHz to communicate with the RFID tag.

56. The process of claim 55, wherein the radio frequency used to communicate with the RFID tag is approximately 13.56 MHz.

57. A process for manufacturing a radio frequency identification device (RFID) for identifying an implant within a patient, comprising the steps of:
providing an active implantable medical device having a header block;
storing information relating to the patient or the active implantable medical device on an RFID tag;
embedding the RFID tag in the header block of the active implantable medical device, wherein the header block has a leak rate of no more than $10^{-9}$ cubic centimeters per second; and
implanting the active implantable medical device in the patient.

58. The process of claim 57, further comprising the step of associating an X-ray identification tag with the container.

59. The process of claim 57, wherein the active implantable medical device comprises an active implantable medical device including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device, and component parts thereof, including lead wires and abandoned lead wires.

60. The process of claim 57, including using a radio frequency of between 132 kHz and 915 MHz to communicate with the RFID tag.

61. The process of claim 60, wherein the radio frequency used to communicate with the RFID tag is approximately 13.56 MHz.

62. A system for identifying implants within a patient, comprising:
- an implantable lead wire;
- a radio frequency identification (RFID) tag associated with the lead wire, the RFID tag containing information relating to the patient, the implantable lead wire, or an implantable medical device connected to the lead wire, wherein the RFID tag is disposed within a hermetically sealed container which is biocompatible and has a leak rate of no more than $10^{-9}$ cubic centimeters per second; and
- an interrogator capable of communicating with the RFID tag.

63. The system of claim 62, wherein the implantable lead wire is connected to an implantable medical device.

64. The system of claim 63, wherein the RFID tag contains information related to the implantable medical device.

65. The system of claim 62, wherein the RFID tag contains information related to the MRI compatibility of the lead wire.

66. The system of claim 62, wherein the hermetically sealed container has a leak rate of no more than $10^{-12}$ cubic centimeters per second.

67. The system of claim 62, wherein a radio frequency of between 132 kHz and 915 MHz is used to communicate with the RFID tag.

68. The system of claim 67, wherein the radio frequency used to communicate with the RFID tag is approximately 13.56 MHz.

69. A system for identifying implants within a patient, comprising:
- an implanted lead wire;
- a radio frequency identification (RFID) tag associated with the lead wire, the RFID tag containing information relating to the patient and/or the implanted lead wire, wherein the RFID tag is disposed within a hermetically sealed container which is biocompatible and has a leak rate of no more than $10^{-9}$ cubic centimeters per second; and
- an interrogator capable of communicating with the RFID tag.

70. The system of claim 69, wherein the implanted lead wire is an abandoned lead wire not connected to a implanted medical device.

71. The system of claim 69, wherein the RFID tag contains information related to the MRI compatibility of the lead wire.

72. The system of claim 69, wherein the RFID tag is hermetically sealed.

73. The system of claim 69, wherein the hermetically sealed container has a leak rate of no more than $10^{-12}$ cubic centimeters per second.

74. The system of claim 69, wherein a radio frequency of between 132 kHz and 915 MHz is used to communicate with the RFID tag.

75. The system of claim 74, wherein the radio frequency used to communicate with the RFID tag is approximately 13.56 MHz.

76. A system for identifying implants within a patient, comprising:
- an implantable medical device;
- a hermetically sealed radio frequency identification (RFID) tag associated with the implantable medical device, the RFID tag containing information relating to the patient and/or the implantable medical device; and
- an interrogator capable of communicating with the RFID tag;
- wherein the implantable medical device includes a header block and the RFID tag is implanted in the header block, wherein the header block has a leak rate of no more than $10^{-9}$ cubic centimeters per second.

77. The system of claim 76, wherein the implantable medical device comprises an active implantable medical device including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires or abandoned lead wires.

78. The system of claim 76, wherein the RFID tag includes an antenna.

79. The system of claim 76, wherein the RFID tag is read-only or readable/writable.

80. The system of claim 78, wherein the interrogator is a read only or a reader/writer device.

81. The system of claim 76, wherein the interrogator is in communication with a computer or computer network.

82. The system of claim 76, wherein a radio frequency of between 132 kHz and 915 MHz is used to communicate with the RFID tag.

83. The system of claim 82, wherein the radio frequency used to communicate with the RFID tag is approximately 13.56 MHz.

84. A system for identifying implants within a patient, comprising:
- an active implantable medical device;
- a hermetically sealed radio frequency identification (RFID) tag associated with the active implantable medical device, the RFID tag including an antenna and containing information relating to the patient and/or the active implantable medical device, wherein the RFID tag is read-only or readable/writable; and
- an interrogator capable of communicating with the RFID tag;
- wherein the active implantable medical device includes a header block and the RFID tag is implanted in the header block, wherein the header block has a leak rate of no more than $10^{-9}$ cubic centimeters per second.

85. The system of claim 84, wherein a radio frequency of between 132 kHz and 915 MHz is used to communicate with the RFID tag.

86. The system of claim 85, wherein the radio frequency used to communicate with the RFID tag is approximately 13.56 MHz.

* * * * *